United States Patent [19]

Lemmen

[11] Patent Number: 5,327,902

[45] Date of Patent: Jul. 12, 1994

[54] APPARATUS FOR USE IN NERVE CONDUCTION STUDIES

[76] Inventor: Roger D. Lemmen, 1241 Heather Dr., Holland, Mich. 49423

[21] Appl. No.: 61,798

[22] Filed: May 14, 1993

[51] Int. Cl.$^5$ ............................................. A61B 5/05
[52] U.S. Cl. ..................................... 128/734; 128/741
[58] Field of Search .................. 128/639, 644, 733.4, 128/741, 774, 782

[56] References Cited

U.S. PATENT DOCUMENTS

| | | |
|---|---|---|
| 3,881,495 | 5/1975 | Pannozzo et al. . |
| 4,341,221 | 7/1982 | Testerman . |
| 4,595,018 | 6/1986 | Rantala ............................ 128/741 X |
| 4,774,967 | 10/1988 | Zanakis et al. . |
| 4,807,643 | 2/1989 | Rosier . |
| 4,811,742 | 3/1989 | Hassel et al. ....................... 128/733 |
| 4,817,628 | 4/1989 | Zealear et al. . |
| 5,012,820 | 5/1991 | Meyer . |
| 5,107,853 | 4/1992 | Plyter . |
| 5,163,443 | 11/1992 | Fry-Welch et al. . |
| 5,215,100 | 6/1993 | Spitz et al. ........................ 128/741 |

*Primary Examiner*—Angela D. Sykes
*Attorney, Agent, or Firm*—Price, Heneveld, Cooper, DeWitt & Litton

[57] ABSTRACT

An apparatus for use in nerve conduction studies includes a fixture for supporting a reference electrode, a recording electrode, a cathode and an anode with the distance between the cathode and the recording electrode being preselected and fixed. The electrodes of the fixture are electrically connected to a nerve stimulator and a controller. A panel and display are connected to the controller along with a storage device and a keyboard input device. A ground pad including a ground electrode and a temperature sensor are connected to the controller. The controller causes an electrical pulse to be transmitted to the cathode. The distal latency and amplitude of the supramaximal stimulus response of the nerve being tested are determined and displayed.

29 Claims, 4 Drawing Sheets

APPARATUS FOR USE IN NERVE CONDUCTION STUDIES

BACKGROUND OF THE INVENTION

The present invention relates to a method and apparatus for performing sensory nerve conduction studies.

Sensory nerve conduction studies are often used by neurologists to diagnose different forms of nerve compression syndrome. Diminished conduction velocity may indicate nerve damage. Such studies may also be used to indicate the development or onset of an abnormal condition. Such studies could, therefore, be used to permit corrective action to be undertaken before permanent damage to the nerve occurs.

In one example, nerve conduction studies could be used to diagnose or determine the potential for or the onset of carpal tunnel syndrome. Carpal tunnel syndrome is a painful condition associated with repetitive use of the hands and wrists. The condition is caused by compression of the median nerve as it passes through the carpal tunnel. Carpal tunnel syndrome is characterized by pain and paresthesia in the sensory distribution of the median nerve in the hand. Symptoms include numbness, tingling and a painful burning sensation in the fingers which can radiate up the forearm to the shoulder.

Heretofore, nerve conduction velocity measurements have been made by stimulating the peripheral nerve with an electrical impulse and measuring the time or latency from the stimulation until an action potential occurs in a muscle innervated by the nerve under examination. Measurements are made by the use of surface electrodes positioned over the muscle that picks up the signals which are then amplified and displayed on a screen of a cathode ray tube or an oscilloscope. Measurements of the distance between the stimulus and response, which peak on the screen of the oscilloscope, are converted into latency times. This technique is referred to as electromyography (EMG). U.S. Pat. No. 4,291,705 entitled NEUROMUSCULAR BLOCK MONITOR, which issued on Sep. 29, 1981 to Severinghaus et al, and U.S. Pat. No. 4,807,643 entitled DIGITAL ELECTRONEUROMETER, which issued on Feb. 28, 1989 to Rosier, disclose methods and apparatus for performing conduction studies, the disclosure of which are hereby incorporated by reference.

EMG generally requires sophisticated and expensive equipment. The studies are typically performed by highly trained medical personnel or technicians. Proper procedures must be followed or error will be present in the results. For example, in conducting a median nerve sensory fiber conduction study, the distance between the stimulating cathode and the recording electrode is critical to obtaining results which may be compared with generally accepted standards or norms. Another source of error involves ambient temperature. Lower temperature will reduce the conduction velocities. In addition, it is important that the electrodes be placed properly on the subject so that the appropriate nerve and responses to stimulation are accurately recorded.

A need exists for apparatus which eliminates measurement errors and assists in the proper placement of electrodes for nerve conduction studies. In addition, a need exists for apparatus which permits nonmedical personnel to conduct studies on a regular basis at reduced cost and with accurate results.

SUMMARY OF THE INVENTION

In accordance with the present invention, the aforementioned needs are fulfilled. An apparatus is provided which includes a fixture for accurately positioning the electrodes used in nerve conduction studies. The fixture includes an elongated body supporting a first pair of electrodes and a second pair of electrodes. The first pair includes a reference electrode and a recording electrode. The second pair includes a stimulating electrode or cathode and an anode. The distance between the cathode and the recording electrode is preselected for the specific nerve conduction study being undertaken in order to eliminate measurement error.

In narrower aspects of the invention, the fixture may include provision for movably mounting the reference and recording electrodes so that the distance between the recording electrode and the stimulating cathode may be changed. In addition, it is preferred that the fixture permit angular positioning of the anode with respect to the cathode.

Operating controls may be positioned on the fixture. The fixture is connected to a nerve stimulator and a controller. A ground electrode and a temperature sensor are preferably connected to the controller. The apparatus generates electrical impulses which are transmitted to the cathode. The potential sensed by the recording and reference electrodes are received by the controller. The voltage level of the impulse is increased until supramaximal stimulus is reached. The controller is connected to a display which presents the amplitude and distal latency associated with the response by the stimulated nerve.

In narrower aspects of the invention, it is preferred that the controller generate a set of instructions presented at the display for the operator to follow in the performing of the specific nerve conduction study. The apparatus is conduction study specific which reduces the extent of training necessary and helps insure accuracy.

The apparatus in accordance with the present invention eliminates common sources of error in conventional nerve conduction studies. The apparatus generates readily comparable data. The apparatus permits the performance of studies on a regular basis to determine the onset of nerve compression syndrome, such as carpal tunnel syndrome.

DETAILED DESCRIPTION OF THE PREFERRED EMBODIMENT

Figure 1:
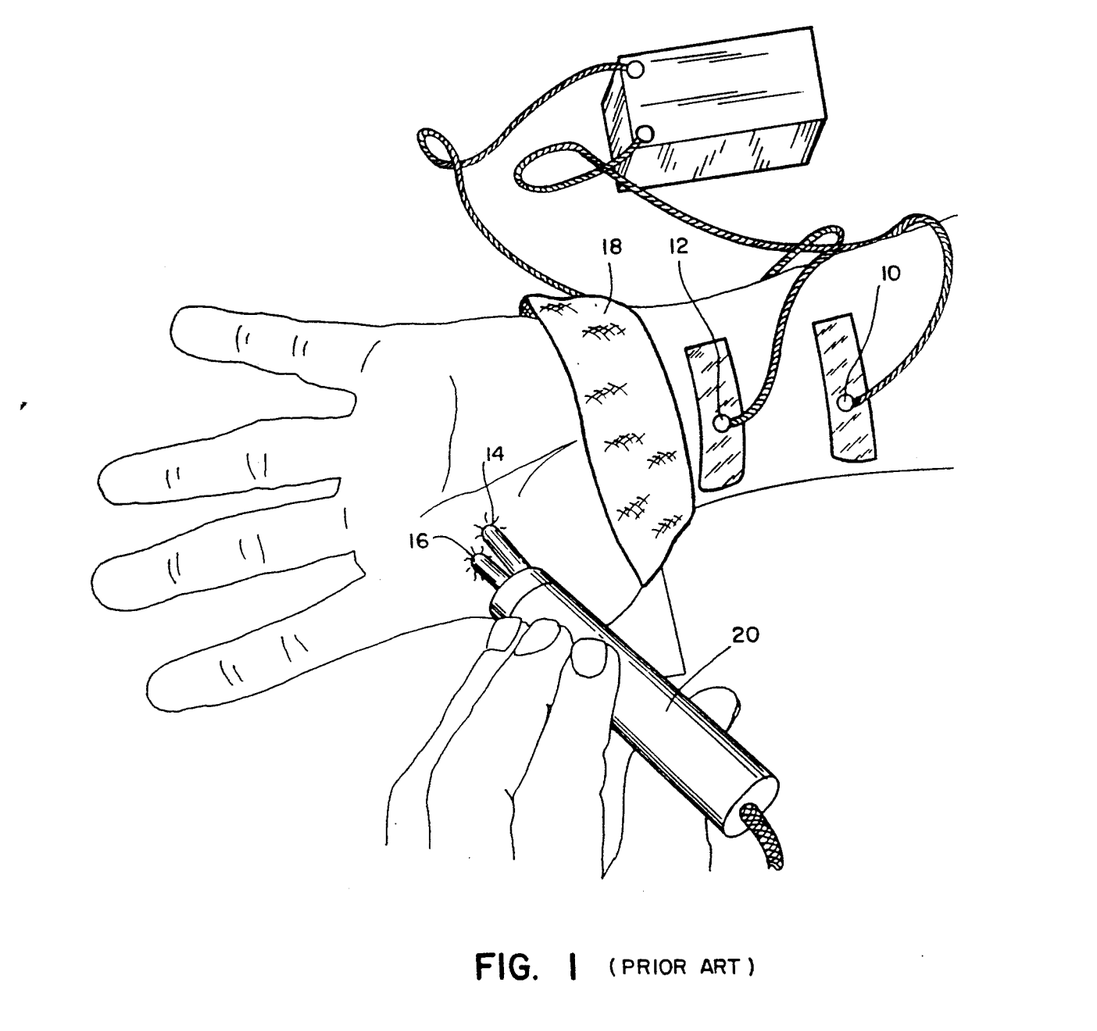
FIG. 1 is a view of the lower arm, wrist and hand of a subject showing the prior art placement of electrodes in the performing of a median nerve sensor fiber conduction study.

Fiber conduction studies have required the placement of a reference electrode 10, commonly referred to as electrode G2, and a recording electrode 12, commonly referred to as G1, on the skin surface. FIG. 1 illustrates electrode placement for a median nerve conduction study. Electrodes G1 and G2 are positioned approximately 3.5 cm apart on the volar surface of the wrist between the flexor carpi radialis and the palmaris longus tendons. Electrodes 14, 16 are positioned on the palm. Palm electrode 14 is the cathode and electrode 16 is the anode. The cathode is positioned along a line that is defined by the web space between the second and third digits and the thumb side of the right wrist just lateral to the flexor carpi radialis tendon. Cathode 14 is positioned 8 cm from the recording electrode 12. A ground electrode is secured to the wrist by a strap 18. The ground electrode is used to minimize or eliminate electrical noise during the measurement.

In prior approaches, electrodes 14, 16 are positioned by a hand-held device 20. Electrodes 14, 16 of device 20 are connected to an EMG apparatus, as are electrodes G1, G2 and ground. Errors in studies using existing equipment result from improper distance measurement and placement of electrodes 10 and 12 with respect to each other and electrodes 12 and 14 with respect to each other. Distance errors on the order of 0.15 ms/cm in the measured distal latency are typical. In addition, low temperatures at the extremity are a source of error. As temperatures decrease, the conduction velocities decrease. The rate of change is on the order of 0.1 ms/c°.

Figures 2, 3:
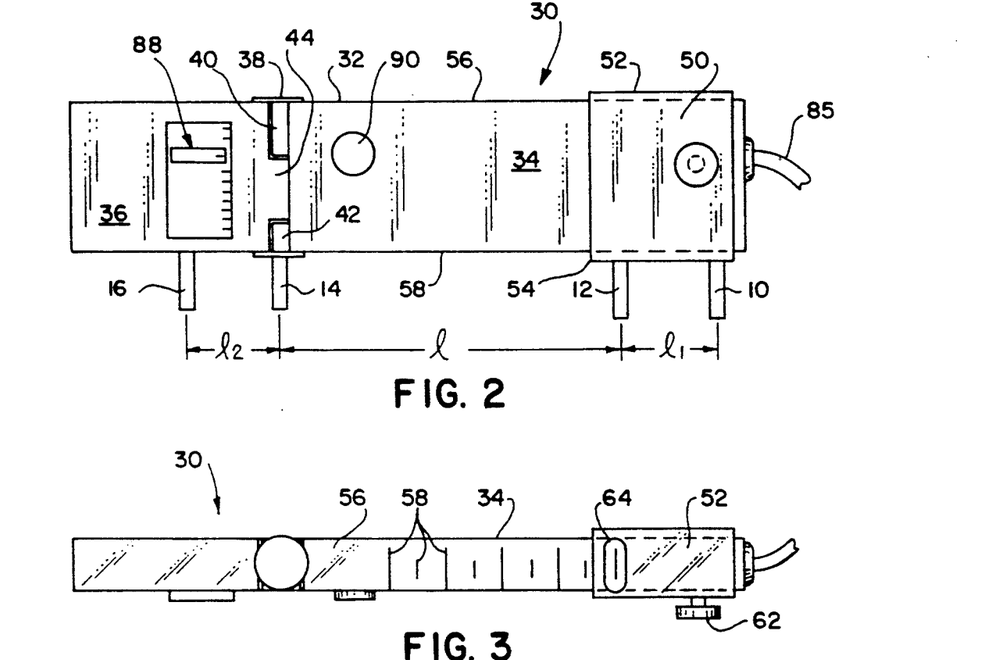
FIG. 2 is an elevational view of a fixture in accordance with the present invention.
FIG. 3 is a top plan view of the fixture of FIG. 2.

In accordance with the present invention, a fixture 30 is provided for properly positioning electrodes 10, 12, 14 and 16. Fixture 30 includes an elongated body 32. Body 32 includes a first portion 34 and a second portion 36. Portions 34 and 36 are hingedly interconnected by a hinge pin 38. Pin 38 extends through portions 40, 42 on body 34 and portion 44 on body portion 36. In the preferred form, cathode 14 is fixed to body 30 at the vertical hinge axis defined by pin 38 and portions 40, 42 and 44. In the presently preferred form, electrodes 10, 12 are mounted on body portion 34 by a slide 50. Slide 50 includes a top flange 52 and a bottom flange 54 which are extended over upper and lower edges 56, 58 of body portion 34. Electrodes 10, 12 are fixed to flange 54 of slide 50. As seen in FIG. 3, an upper surface 56 of body portion 4 is formed with gradations or tick marks 58. The tick marks are calibrated to indicate the distance 1 between the recording electrode 12 and cathode 14. Slide 50 is fixed in position by a set screw 62. Upper flange 52 defines a window or aperture 64 which permits the gradations 58 to be read. Slide 50 mounts electrodes 10, 12 at a distance $1_1$. Electrodes 14, 16 are mounted a preselected distance $1_2$ with respect to each other. The distance $1_1$ between recording electrode 12 and stimulating cathode or electrode 14 is preselected and corresponds to that needed for the type of study being conducted. Electrodes 10, 12, 14 and 16 are connected through fixture 30 to a conductor within a cord 85. In addition, fixture 30 may include a rheostat or variable position slide potentiometer 88 to control the voltage levels applied to the stimulating electrode as discussed below. Further, a storage actuating switch 90 may be mounted on the fixture for ready use by the operator in conducting a study.

Figure 4:
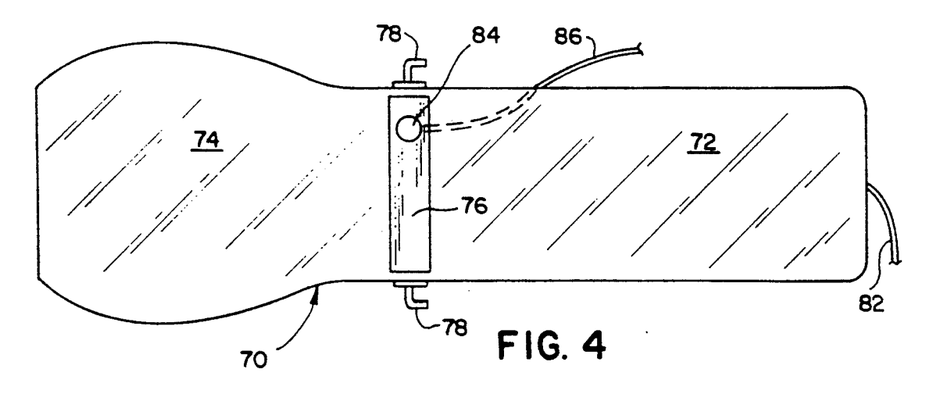
FIG. 4 is a plan view of a ground pad and electrode incorporated in the present invention.

FIG. 4 illustrates a ground pad usable with the fixture 30 of FIGS. 2 and 3. Pad 70 includes a planar, elongated wrist and forearm support portion 72 and a hand and wrist support portion 74. A raised ground electrode 76 is fixed to pad 70 adjacent the wrist area of the subject. Hooks 78 extend from the side of pad 70. The hooks provide a place for attachment of an elastic strap or band to secure the subject's forearm, wrist and hand in position on pad 70. Ground electrode 76 is connected to an electrical lead 82. In addition, a thermistor 84 or other temperature sensor is mounted on ground electrode 76. Sensor 84 is electrically connected to a lead 86.

Figure 5A:
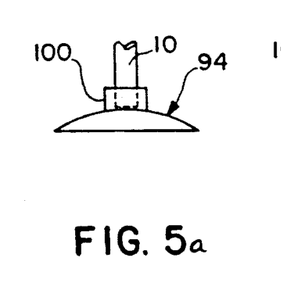
FIGS. 5a, 5b and 5c are elevational views of alternative electrode attachment devices which may be used with the present invention.
Figure 5B:
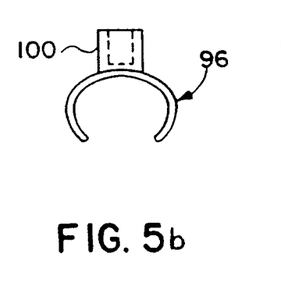
Figure 5C:
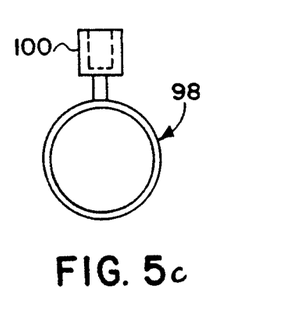

Various devices may be used in connection with the electrodes to attach them to the subject. As shown in FIG. 5a, a conventional bipole or surface disk 94 may be attached to any of the electrodes. A ring attachment structure 96, as shown in FIG. 5b, may also be used. A loop attachment structure 98, as shown in FIG. 5c, may further be used. Each of the devices 94, 96 and 98 includes an attachment stem portion 100 dimensioned to receive the electrode. The various types of attachment structures are provided depending upon the type of nerve conduction study being performed. When conducting a median nerve sensory fiber conduction study to position the electrodes as shown, for example, in FIG. 1, disks 94 would typically be used.

Figure 6:
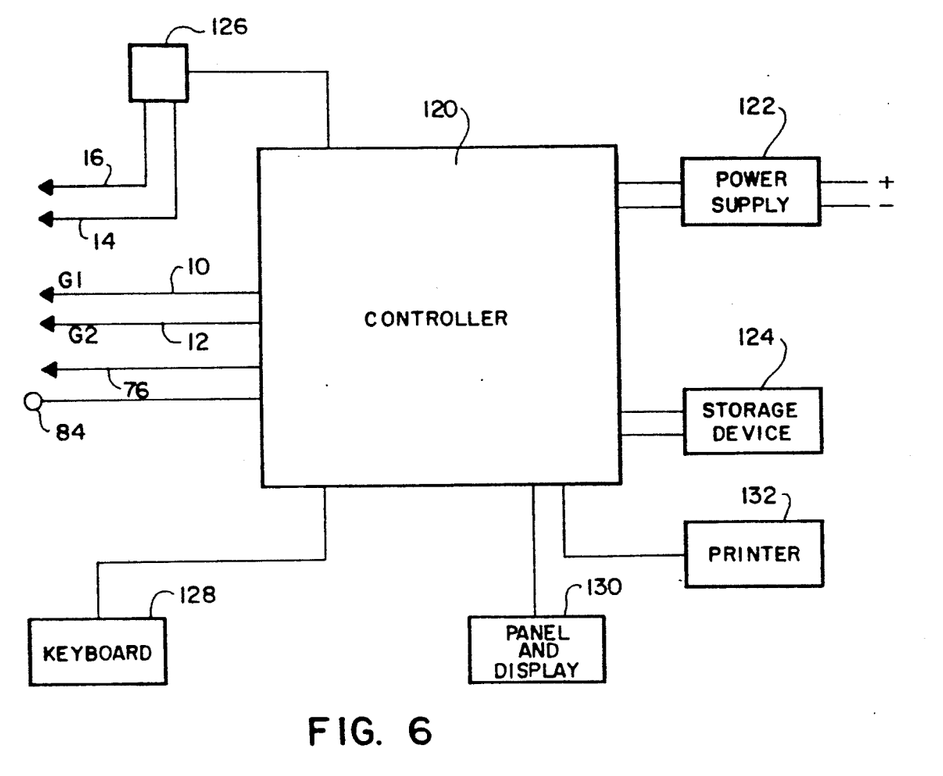
FIG. 6 is a schematic view of an electrical controller, display and related apparatus in accordance with the present invention.

Electrodes 14, 16, 10, 12, 76 and temperature sensor 84 are connected to a controller 120, as schematically illustrated in FIG. 6. Controller 120 is a programmable device which is also connected to a power supply 122, a disk or data storage device 124, a nerve stimulator 126, a keyboard input device 128, a panel and display device 130 and a printer 132. Controller 120 controls the application of an electrical impulse from the nerve stimulator 126 to cathode 14. Controller 120 also receives the electrical output signals from electrodes 10, 12 and processes the information to present an appropriate display of amplitude and distal latency at the panel and display 130. As discussed below, keyboard 128 is used to input data about the subject to the controller for permanent recording in connection with the test results.

Figure 7:
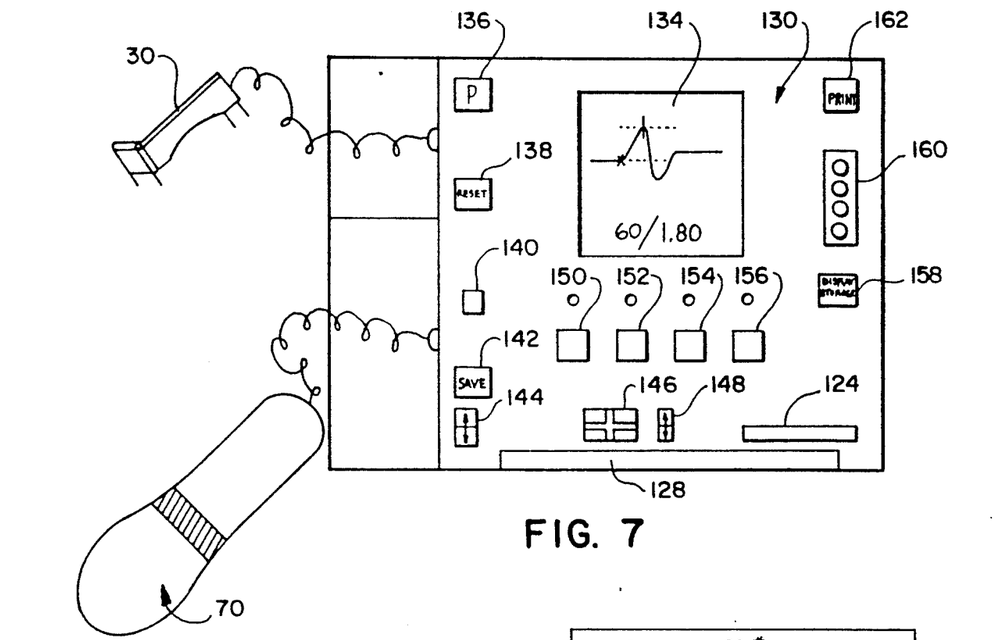
FIG. 7 is a plan view of an apparatus in accordance with the present invention including a control panel and display, fixture and ground pad.

As best seen in FIG. 7, panel and display 130 includes an oscilloscope with a cathode ray tube display 134, a power on switch 136, a reset switch 138, a temperature switch 140, a save switch 142, a gain indicator (up/down) 144, a cursor control 146, an up/down indicator 148, specific conduction study indicator buttons 150, 152, 154 and 156, and a display storage button 158. Controls 160 for the CRT display 134 are provided. A print button 162 is also included. Keyboard 128 is storable beneath the panel. In addition, the storage device 124 includes an access slot for a standard magnetic disk. FIG. 7 schematically illustrates the attachment of fixture 30 and ground pad 70 to the controller.

The apparatus illustrated in FIGS. 6 and 7 is designed for performing nerve conduction studies which measure distal latencies in the median nerve sensory fiber. Such studies are usable to determine the presence or possible onset of carpal tunnel syndrome.

In operation, the user would turn on power to the apparatus by pushing button 136. Reset button 138 would be pressed to clear unwanted information from the programmable controller. The temperature sensor 84, pad 70 and ground electrode 76 would be positioned on the hand of the patient. An elastic band is secured to hooks 78 to insure that the back of the wrist is placed against electrode 76 and sensor 84. Temperature switch 140 is pressed to record the temperature of the extremity sensed by thermistor 84. Controller 120 may be programmed to use such information in generating output values which are temperature corrected.

It is presently preferred that the controller be programmed to generate test instruction procedures which are displayed on the CRT 134 for user operation. The instructions prompt the operator to input the date, name, age and other appropriate identifying information concerning the individual into the apparatus using the keyboard 128. Such information is stored and permanently recorded along with the results of the conduction studies and printed on an appropriate hard copy printout.

Next the operator is instructed to activate the appropriate switch for the particular conduction study being performed. In the form illustrated in FIG. 7, button 150 is designated RMS for right median sensory. Button 152 is designated RUS for right ulnar sensory. Button 154 is designated LMS for left median sensory, and button 156 is designated LUS for left ulnar sensory.

The operator will have been previously trained to apply the electrode fixture 30 to obtain the right median sensory response initially. The cathode is positioned along the lines defined by the web space between the second and third digits on the thumb side of the right wrist, just lateral to the flexor carpi radialis tendon. The fixture is positioned over the hand, which is positioned as shown in FIG. 1, so that electrodes 10 and 12 are in the appropriate places and electrodes 14, 16 are properly positioned. Once the electrode fixture is positioned, the operator will increase the voltage of the stimulus using slide 88 and electric shocks will be emitted through the cathode every second. As the voltage increases by moving slide or rheostat 88, the amplitude of the output sensed by electrodes 10, 12 will also increase. At the point where the amplitude does not increase any further even though the voltage has been increased an additional increment, supramaximal stimulus of the median nerve has been reached. Anode 14 is then rotated angularly with respect to cathode 14 so that the base line of the response as displayed on the CRT 134 is essentially horizontal. Once an acceptable response is obtained, the operator activates the capture or save button 90 on fixture 30 so that the response will be held and displayed at the CRT tube.

The operator then uses the cursor controls 146, 148 to determine amplitude and distal latency. Switch 148 is placed in its lower station. As a result, movement of the cursor will be along the X axis along the response. The cursor is then positioned to set the base of the amplitude response. Switch 148 is then moved to the upper position. The cursor is then elevated using cursor control 146 until it reaches the top of the response, as schematically illustrated by the dotted lines in FIG. 7. The controller will then display a number under the response. The number indicates the numerical value of the amplitude. The cursor control 146 is again used to position the cursor until a vertical line displayed hits the central, peak portion of the response and which is to be measured. The controller uses this information to generate and display the distal latency in milliseconds. The amplitude is preferably displayed in microvolts. As shown, the display is in the form amplitude value/distal latency value.

Figure 8:
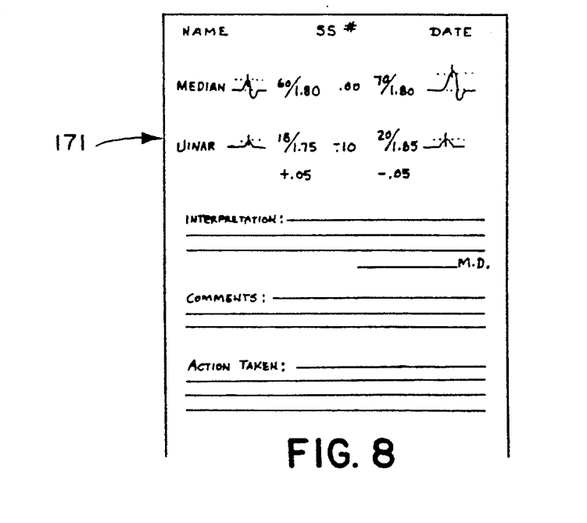
FIG. 8 is a representative printed output from the subject apparatus.

In order to properly place the cursors, the responses need to be the appropriate height. If the response is too high, one can decrease the gain or sensitivity by pushing the button 144 below the save button 142. If the response is too low, one could also increase the gain or sensitivity. When the recorded response is considered appropriate, the save button 142 is pressed and a light above a button 150 will light up indicating that a response has been stored safely for that testing factor. The procedure is then repeated pursuant to instructions displayed on screen 134 to determine RUS, LMS and LUS. When responses are appropriately obtained, all of the lights above the buttons 150, 152, 154 and 156 will be displayed. All responses can be displayed on the CRT tube for evaluation. In addition, the controller will display or generate the variances or differences between the distal latencies comparing the right median to the right ulnar, the left median to the left ulnar and also right median to left median responses and right ulnar to left ulnar responses. Normal values include median sensory nerve action potential amplitudes of 50 or more microvolts, ulnar sensory action potential amplitudes of 15 or more microvolts, with variance determinations being normal up to 0.2 ms when comparing median and ulnar responses of the ipsilateral arm and median to median and ulnar to ulnar responses of contra lateral arms. The variances are preferably determined, however, only for distal latencies which should be up to and including 2.2 ms with regard to median sensory distal latencies using the palmer method and up to 2.2 ms with regard to ulnar sensory distal latencies using the palmer method. Noted abnormalities would be highlighted on the display screen for easy reference. Once all responses are properly recorded, display storage button 158 may be pushed, which will store the information permanently on a recording medium. This information will be permanently recorded along with the individual patient or subject information. Print button 162 may be pressed to generate a printed output 171, as shown, for example, in FIG. 8. Once information is properly recorded and stored, the apparatus may be prepared for further testing. The fixture and base electrodes need to be wiped off conveniently with an alcohol wipe or the like. Appropriate cleaning measures would be taught to the operator.

The controller which generates the instructions and the fixture 30 permit the apparatus to be used by nonmedical personnel or personnel with limited training. Sources of error such as that caused by temperature and placement of electrodes are eliminated. The apparatus permits specific nerve conduction studies to be regular or repetitively conducted to determine onset or the presence of a compressive nerve disorder. Appropriate screening for potential carpal tunnel syndrome may be undertaken and corrective action initiated. Work and disability problems could be reduced or more quickly treated.

In view of the above description, those of ordinary skill in the art may envision various modifications which would not depart from the inventive concepts disclosed herein. It is expressly intended, therefore, that the above description should be considered as only that of the preferred embodiment. The true spirit and scope of the present invention may be determined by reference to the appended claims.

The embodiments of the invention in which an exclusive property or privilege is claimed are defined as follows:

1. A hand held fixture for use in nerve conduction studies, said fixture comprising:
   an elongated body having a first portion, a second portion, an upper edge and a lower edge;
   a first pair of electrodes mounted on the lower edge of said body adjacent an end of said first portion, one of said electrodes being a reference electrode and the other of said electrodes being a recording electrode;
   a second pair of electrodes fixed to said body on the lower edge thereof, one of said second pair of electrodes being a cathode and the other of said electrodes of said second pair being an anode, said anode being fixed to said second portion of said body; and
   adjustment means on said body for adjustably mounting said recording electrode and said cathode with respect to each other so that a distance "1" between the recording electrode and cathode may be changed and fixed for the type of nerve conduction study being performed.

2. A fixture as defined in claim 1 wherein said first portion and said second portion of said body are hingedly interconnected along a vertical axis so that said second portion may be rotated about said axis.

3. A fixture as defined by claim 2 wherein said cathode is fixed to said body at said vertical axis so that as said second portion is rotated the angular position of said anode with respect to said cathode may be changed without changing the distance "1" between said cathode and said recording electrode.

4. A fixture as defined y claim 1 further comprising: switch means on said body for activating storage of responses to nerve stimulation.

5. A fixture as defined by claim 1 further comprising: a rheostat on said body for adjusting the voltage level of pulses applied to the cathode.

6. A fixture for use in nerve conduction studies, said fixture comprising:
   an elongated body having a first portion, a second portion, an upper edge and a lower edge;
   a first pair of electrodes mounted on the lower edge of said body adjacent an end of said first portion, one of said electrodes being a reference electrode and the other of said electrodes being a recording electrode;
   a second pair of electrodes fixed to said second portion of said body on the lower edge thereof, one of said second pair of electrodes being a cathode and the other of said electrodes of said second pair being an anode, the distance between the cathode and said recording electrode being fixable and at a distance predetermined for the type of nerve conduction study being conducted; and
   slide means on said body for slideably and adjustably mounting said first pair of electrodes on said body so that the distance "1" between the cathode and recording electrode can be changed within predetermined limits.

7. A fixture for use in nerve conduction studies, said fixture comprising:
   an elongated body having a first portion, a second portion, an upper edge and a lower edge;
   a first pair of electrodes mounted on the lower edge of said body adjacent an end of said first portion, one of said electrodes being a reference electrode and the other of said electrodes being a recording electrode;
   a second pair of electrodes fixed to said second portion of said body on the lower edge thereof, one of said second pair of electrodes being a cathode and the other of said electrodes of said second pair being an anode, the distance between the cathode and said recording electrode being fixable and at a distance predetermined for the type of nerve conduction study being conducted;
   a rheostat on said body for adjusting the voltage level of pulses applied to the cathode; and
   slide means on said body for slideably and adjustably mounting said first pair of electrodes on said body so that the distance "1" between the cathode and recording electrode can be changed within predetermined limits.

8. A fixture as defined by claim 7 further comprising: switch means on said body for activating storage of responses to nerve stimulation.

9. A fixture as defined by claim 8 wherein said first portion and said second portion of said body are hingedly interconnected along a vertical axis.

10. A fixture as defined by claim 9 wherein said cathode is fixed to said body at said vertical axis so that the angular position of said anode with respect to said cathode may be changed without changing the distance "$1_2$" between said anode and said cathode and the distance "$1_1$" between said cathode and said recording electrode.

11. An apparatus for performing nerve sensory fiber conduction studies comprising:
    an electrode fixture having a reference electrode, a recording electrode, a cathode and an anode, said fixture further including adjustment means thereon for adjustably setting and fixing the distance between said recording electrode and said cathode in accordance with the type of study being performed;
    a ground electrode;
    a temperature sensor;
    a nerve stimulator electrically connected to said cathode and anode;
    an operator panel including a display; and
    controller means connected to said reference and recording electrodes, said cathode, said anode, said ground electrode, said temperature sensor, said nerve stimulator and said panel and display for delivering a controlled electrical impulse to said cathode, measuring the response thereto as sensed by the recording electrode and generating an output which represents the amplitude and distal latency of the response.

12. An apparatus as defined by claim 11 further comprising:
    an input means connected to said controller means for inputting information on the subject of the study.

13. An apparatus as defined by claim 12 further comprising:
    a storage means for recording and storing said output and said information on the subject.

14. An apparatus as defined by claim 13 wherein said display is a cathode ray tube.

15. An apparatus as defined by claim 11 wherein said operator panel includes switches labeled for specific nerve conduction studies and said controller means generates a step-by-step procedure on the display for an operator when one of said switches is actuated.

16. An apparatus as defined by claim 15 further comprising:

an input means connected to said controller means for inputting information on the subject of the study.

17. An apparatus as defined by claim 16 further comprising
a storage means for recording and storing said output and said information on the subject.

18. An apparatus as defined by claim 17 wherein said electrode fixture comprises:
an elongated body having ends, said reference and recording electrodes being fixed to said body and said anode and cathode being fixed to said body with the distance "1" between the cathode and recording electrode being fixed for the type of nerve conduction study being performed.

19. An apparatus as defined by claim 18 further comprising:
a pad, said ground electrode and said temperature sensor being fixed to said pad.

20. An apparatus as defined by claim 19 wherein said elongated body of said fixture includes a first portion hinged to a second portion about a hinge axis and wherein said recording and reference electrodes are mounted on said first portion, said cathode is positioned on said hinge axis and said anode is fixed to said second portion.

21. An apparatus as defined by claim 11 wherein aid electrode fixture comprises:
an elongated body having ends, said reference and recording electrodes being fixed to said body by said adjustment means and said anode and cathode being fixed to said body with the distance "1" between the cathode and recording electrode being predetermined and fixed for the type of nerve conduction study being performed.

22. An apparatus as defined by claim 21 further comprising:
a pad, said ground electrode and said temperature sensor being fixed to said pad.

23. An apparatus as defined by claim 22 wherein said elongated body of said fixture includes a first portion hinged to a second portion about a hinge axis and wherein said recording and reference electrodes are mounted on said first portion, said cathode is positioned on said hinge axis and said anode is fixed to said second portion.

24. An apparatus for performing nerve sensory fiber conduction studies comprising:
an electrode fixture having a reference electrode, a recording electrode, a cathode and an anode, said fixture setting the distance between said recording electrode and said cathode;
a ground electrode;
a temperature sensor;
a nerve stimulator electrically connected to said cathode and anode;
an operator panel including a display;
controller means connected to said reference and recording electrodes, said cathode, said anode, said ground electrode, said temperature sensor, said nerve stimulator and said panel and display for delivering a controlled electrical impulse to said cathode, measuring the response thereto as sensed by the recording electrode and generating an output which represents the amplitude and distal latency of the response, said electrode fixture comprising:
an elongated body having ends, said reference and recording electrodes being fixed to said body and said anode and cathode being fixed to said body with the distance "1" between the cathode and recording electrode being predetermined and fixed for the type of nerve conduction study being performed; and
a pad, said ground electrode and said temperature sensor being fixed to said pad, said elongated body of said fixture including a first portion hinged to a second portion about a hinge axis and wherein said recording and reference electrodes are mounted on said first portion, said cathode is positioned on said hinge axis and said anode is fixed to said second portion, and wherein said fixture further comprises:
a slide movable along said first portion of said fixture elongated body, said recording and reference electrodes being mounted on said slide.

25. An apparatus for performing nerve sensory fiber conduction studies comprising:
an electrode fixture having a reference electrode, a recording electrode, a cathode and an anode, said fixture setting the distance between said recording electrode and said cathode;
a ground electrode;
a temperature sensor;
a nerve stimulator electrically connected to said cathode and anode;
an operator panel including a display;
controller mean connected to said reference and recording electrodes, said cathode, said anode, said ground electrode, said temperature sensor, said nerve stimulator and said panel and display for delivering a controlled electrical impulse to said cathode, measuring the response thereto as sensed by the recording electrode and generating an output which represents the amplitude and distal latency of the response, said operator panel including switches labeled for specific nerve conduction studies and said controller means generates a step-by-step procedure on the display for an operator when one of said switches is actuated, an input means connected to said controller means for inputting information on the subject of the study;
a storage means for recording and storing said output and said information on the subject, said electrode fixture comprising:
an elongated body having ends, said reference and recording electrodes being fixed to said body and said anode and cathode being fixed to said body with the distance "1" between the cathode and recording electrode being fixed for the type of nerve conduction study being performed; and
a pad, said ground electrode and said temperature sensor being fixed to said pad, wherein said elongated body of said fixture includes a first portion hinged to a second portion about a hinge axis and wherein said recording and reference electrodes are mounted on said first portion, said cathode is positioned on said hinge axis and said anode is fixed to said second portion, and wherein said fixture further comprises:
a slide movable along said first portion of said fixture elongated body, said recording and reference electrodes being mounted on said slide.

26. A device for use in nerve conduction studies, said device comprising:
an elongated body having a first portion, a second portion, an upper edge and a lower edge;

a first pair of electrodes mounted on the lower edge of said body adjacent an end of said first portion, one of said electrodes being a reference electrode and the other of said electrodes being a recording electrode; and a second pair of electrodes fixed to said body on the lower edge thereof, one of said second pair of electrodes being a cathode and the other of said electrodes of said second pair being an anode, said anode being fixed to said second portion of said body, the distance between the cathode and said recording electrode being fixed at a distance predetermined for the type of nerve conduction study being conducted, said first portion and said second portion of said body being hingedly interconnected along a vertical axis and wherein said cathode is fixed to said body at said vertical axis so that the angular position of said anode with respect to said cathode may be changed without changing a distance "1" between said cathode and said recording electrode and a distance "1$_2$" between the anode and cathode.

27. A device as defined by claim 26 further comprising:

a nerve stimulator electrically connected to said cathode and anode; and controller means connected to said nerve stimulator for delivering a controlled electrical impulse to said cathode, measuring the response thereto as sensed by the recording electrode and generating an output.

28. A device as defined by claim 27 further comprising:

a ground electrode;

a temperature sensor; and a pad, said ground electrode and said temperature sensor being mounted on said pad and electrically connected to said controller means.

29. A device as defined by claim 26 further comprising:

adjustment means on said elongated body for moveably positioning said recording electrode with respect to said cathode to set the distance "1" therebetween in accordance with the type of study being conducted.

* * * * *